United States Patent [19]

Igarashi

[11] Patent Number: 5,296,194
[45] Date of Patent: Mar. 22, 1994

[54] BLOOD ANALYZING SYSTEM
[75] Inventor: Kenichi Igarashi, Tatebayashi, Japan
[73] Assignee: Sanyo Electric Co., Ltd., Osaka, Japan
[21] Appl. No.: 824,146
[22] Filed: Jan. 23, 1992
[30] Foreign Application Priority Data
  Feb. 1, 1991 [JP] Japan ................. 3-012118
[51] Int. Cl.$^5$ .................. G01N 1/14; G01N 21/78
[52] U.S. Cl. ................... 422/82.05; 422/100; 73/864.13; 73/864.21; 250/231.14
[58] Field of Search ............... 422/82.05, 100; 436/54; 73/864.11, 864.13, 864.16, 864.21; 250/231.13, 231.14, 229

[56] References Cited

U.S. PATENT DOCUMENTS

| | | | |
|---|---|---|---|
| 3,559,065 | 1/1971 | Grundy | 250/231.14 X |
| 3,886,354 | 5/1975 | Swiden et al. | 250/231.14 X |
| 3,915,651 | 10/1975 | Nishi | 422/100 X |
| 4,345,483 | 8/1982 | Paletta et al. | 73/864.16 |
| 4,399,712 | 8/1983 | Oshikubo et al. | 422/100 X |
| 4,519,258 | 5/1985 | Jakubowicz | 73/864.16 |
| 4,591,568 | 5/1986 | Banno et al. | 436/180 |
| 4,760,939 | 8/1988 | Ball et al. | 422/100 X |
| 4,800,762 | 1/1989 | Sugaya | 73/864.24 |
| 4,855,109 | 8/1989 | Muraishi et al. | 422/82.05 X |
| 4,896,270 | 1/1990 | Kalmakis et al. | 73/864.16 X |
| 4,905,526 | 3/1990 | Magnussen, Jr. et al. | 422/100 X |
| 4,988,482 | 1/1991 | Weston | 422/100 |
| 5,061,639 | 10/1991 | Lung et al. | 422/100 X |

FOREIGN PATENT DOCUMENTS

| | | |
|---|---|---|
| 0055483 | 7/1982 | European Pat. Off. |
| 0194442 | 8/1987 | Japan |
| 0217662 | 2/1990 | Japan |
| WO83/00931 | 3/1983 | World Int. Prop. O. |
| WO91/08463 | 6/1991 | World Int. Prop. O. |

OTHER PUBLICATIONS

Soviet Inventions Illustrated, Section Ch, Week 8209, 14 Apr. 1982 Derwent Publications Ltd., London, GB; SU-A-828 079, G. S. Grinberg, 7 May 1981.

Primary Examiner—James C. Housel
Assistant Examiner—Jeffrey R. Snay
Attorney, Agent, or Firm—Oliff & Berridge

[57] ABSTRACT

A blood analyzing system for analyzing the level of content of a component (such as glucose) of blood collected from a person or animal. In the blood analyzing system, a pipet unit includes a drop meter for measuring the volume of the blood sample actually dropped onto a test slide. Reacting to a reagent coated on the test slide, the blood sample changes its color, which is optically detected. A content calculating circuit calculates the level of content of the blood sample based on the received light signal. The content calculating circuit also corrects the calculated results according to the volume of the actually dropped blood sample.

8 Claims, 3 Drawing Sheets

BLOOD ANALYZING SYSTEM

BACKGROUND OF THE INVENTION

1. Field of the Invention

This invention relates to a blood analyzing system for analyzing the amount of a component such as glucose which is present in a blood sample.

2. Description of the Related Art

The components of blood collected from a man or animal are measured to check his or its health.

The components such as glucose, LHD (lactate dehydrogenase) and neutral fat are usually measured and analyzed for the foregoing purpose. Hereinafter, a component to be measured and analyzed is called the "specified component."

The specified component is usually measured as described below. A drop of a blood sample (e.g. centrifugally separated serum or plasma) is applied onto a glass test slide coated with a reagent on its upper side. Reacting to the reagent, the dropped blood is colored or changes its color. In a certain period of time, light is irradiated onto the test slide. The light reflected from or passing through the test slide is received, so that the level of content of the specified component can be calculated according to intensity of the light having a particular wavelength. One example of measuring instruments for this purpose is disclosed in a Japanese Patent Laid-Open Publication No. Sho 62-194442.

To analyze the component accurately, a known volume of the blood sample should be applied onto the test slide. When it is manually applied by a pipet, the volume of the blood sample will become variable, thereby making the analysis less reliable.

Japanese Utility Model Laid Open Publication No. Hei 2-17662 discloses a pipet unit for applying the blood sample. The pipet unit sucks and transfers the blood sample by the pump action exerted by a piston and a cylinder. The volume of the blood sample can be more accurately controlled than when the sample is manually transferred. In the cited invention, the piston is operated by a piston actuator.

With the conventional pipet unit, the volume of the blood sample actually transferred is not measured at all. If the piston stroke happened to become irregular temporarily or intermittently, the transferred volume of the blood sample would deviate from the present volume. Therefore, it is necessary to correct errors in the analyzed results due to inaccurate volumes of the blood samples.

In addition, the volume of the applied blood sample is variable because the piston stroke sometimes becomes irregular due to backlash resulting from relative motion of gears caused by looseness in the piston actuator. Therefore, it is necessary to remove such backlash as much as possible.

SUMMARY OF THE INVENTION

It is therefore an object of this invention to provide a blood analyzing system which can accurately analyze the level of content of a specified component of the blood sample even when the transferred volume of the blood sample becomes variable.

According to the invention, a pipet unit includes a drop meter. An analyzing unit determines the amount of a specified component in the blood sample referring to the volume of the dropped blood sample.

The drop meter measures the volume of the blood sample actually dropped. The pipet unit also includes a motor, a gear coupled to the motor, a rotor coupled to an output shaft of the gear, and a piston actuator for converting the rotary motion of the rotor to the rectilinear motion. The drop meter detects the rotative amount of the rotor, i.e. piston stroke, to indirectly measure the volume of the dropped blood sample.

A light source supplies light to a test slide on which the blood sample is held. The light reflected from or passing through the test slide is received by an optical sensor. The received light signal and drop volume signal are sent to an analyzing unit, which corrects calculated results according to variations of the dropped volume of the blood sample, determining the level of content of the specified component based on the intensity of the received light signal. Such factors as inputted received light signals and calculation coefficients are corrected as well as the calculated contents.

DETAILED DESCRIPTION

Figure 1:
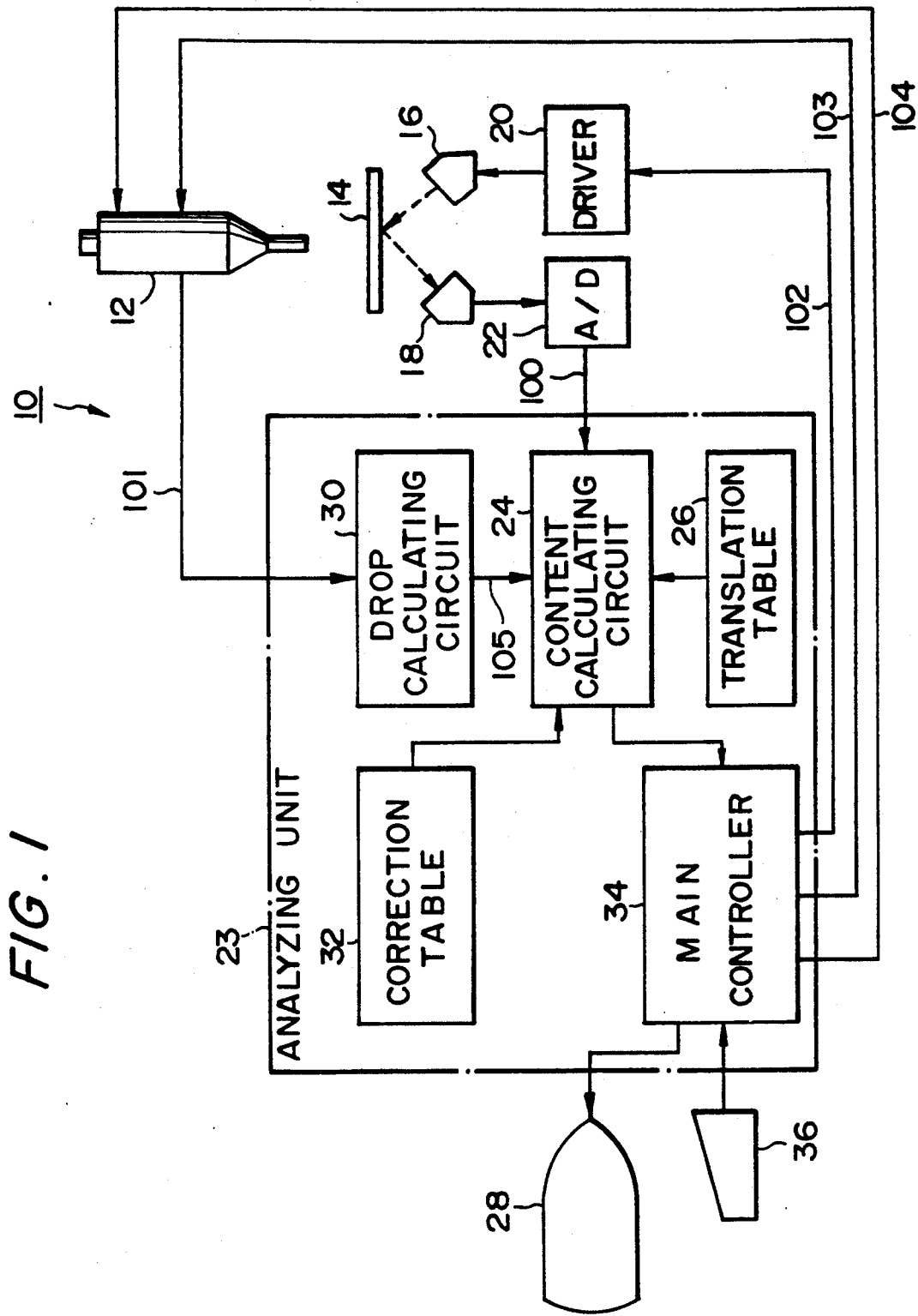
FIG. 1 is a block diagram of a blood analyzing system according to the invention.

The invention will be described with reference to a preferred embodiment shown in the drawing figures.

A blood analyzing system 10 of FIG. 1 is used to measure the amount of a specified component (e.g. glucose) which is present in a blood sample.

A pipet unit 12 transfers a known volume of the blood sample to a test slide 14 from a non-illustrated test tube, being supported manually or on a scanner, not shown. The pipet unit 12 will be detailed later with reference to FIG. 2.

When it is applied to the test slide 14 coated with a reagent, the blood sample changes its color.

Light is irradiated onto the color-changed area of the test slide 14 from a light source 16. The light is reflected from the color-changed blood sample, being received by an optical sensor 18. The optical sensor 18 receives only the light having a particular wavelength corresponding to the changed color, converting the received light to a current having an intensity corresponding to the quantity of the received light, and converting the current to a voltage which is output to an analog to digital converter 22.

A driver 20 supplies a drive signal to the light source 16.

The operation of an analyzing unit 23 will be described hereinafter. A content calculating circuit 24 receives the received light signal 100 from the analog to digital converter 22 to determine the level of content of the specified component in the blood sample. Specifically, the content calculating circuit 24 calculates the amount according to the intensity of the received light signal 100.

A translation table 26 stores the relationship between the intensity of the received light signal and the level of content of the specified component when the known volume of the blood is applied to the analyzing system. Referring to the translation table 26, the content calculating circuit 24 calculates how much glucose (in milligrams) is contained in the blood sample of 1 deciliter, for example.

The content, a calculated result, is indicated on a display 28 via a main controller 34.

The foregoing calculation is performed when the volume of the dropped blood is substantially equal to the predetermined volume.

The following describes the calculation to be carried out when the volume of the dropped blood deviates from the predetermined volume.

The pipet unit 12 outputs a pulse signal 101, which indicates the volume of the dropped blood, to a drop calculating circuit 30. The pulse signal 101 indicates the stroke of a piston of the pipet unit 12, i.e. the volume of the blood actually transferred by the pipet unit 12, as described later.

Receiving the pulse signal 101, the drop calculating circuit 30 counts the pulses in the signal 101 to determine the volume of the dropped blood sample. The drop calculating circuit 30 includes a decoder and a table showing the relationship between the number of the counted pulses and the volume of the dropped blood sample. The decoder and table are not shown in FIG. 1. The drop calculating circuit 30 outputs to the content calculating circuit 24 a signal 105 indicating the calculated drop volume.

The content calculating circuit 24 compares the actual volume indicated by the signal 105 with the predetermined volume. The content calculating circuit 24 corrects its calculated result when the actually dropped volume of the blood sample does not meet the predetermined volume. In other words, the content calculating circuit 24 performs correction of its calculated result if necessary.

Specifically, a correction table 32 stores the relationship between the error (i.e. difference between the predetermined volume and the actually dropped volume) and correction coefficient. Calculating the error, the content calculating circuit 24 determines a correcting coefficient referring to the correction table 32. The content calculating circuit 24 multiplies the calculated result by using the obtained correcting coefficient. The corrected content is sent to the display 28 via the main controller 34.

The foregoing correction is also applicable to the received light signal 100. When the translation table 26 stores the relationship between the intensity of the received light signal 100, the volume of the blood sample actually dropped and the level of content of the component, the foregoing correction can be performed simultaneously with the calculation of the level of content.

The main controller 34 shown in FIG. 1 controls the units constituting the blood analyzing system, being connected to the display 28 and a keyboard 36. The keyboard 36 is operated to renew the contents of the correction and translation tables.

The main controller 34 outputs a light emission control signal 102 to the driver 20, and a detector operating signal 103 and a motor control signal 104 to the pipet unit 12.

As a modification of the foregoing embodiment, it is conceivable that the output signal 105 of the drop calculating circuit 30 is forwarded to the main controller 34 to regulate the drop volume of the blood by means of the feedback control. Specifically, the main controller 34 controls the number of rotations of a motor (to be described later) to determine the proper drop volume according to the difference between the actual drop volume and the predetermined value. Therefore, the drop volume can be kept uniform.

The configuration of the pipet unit 12 will be described with reference to FIG. 2.

A motor 42 is housed in a motor case 40, being applied the motor control signal 104 via a base plate 44. The motor 42 is a DC motor (motor of direct current type) in this embodiment, but may be a stepping motor.

A rotary shaft 42a of the motor 42 is coupled to a gear 46 so that an output shaft 46a is rotated at a reduced velocity. A rotor 50 is coupled to the output shaft 46a via a joint 48.

The rotor 50 is a hollow cylindrical member, having at its bottom a screw hole 50a, through which a feed screw 52 is fitted.

An arm 52a extends from the feed screw 52, having a tip received in a rotation preventing member 55, which allows reciprocation of the feed screw 52 but prevents rotation thereof. In other words, the tip of the arm 52a is fitted into a vertical groove of the rotation preventing member 55 to permit the reciprocation of the feed screw 52.

The motor 42 is set in motion to rotate the rotor 50, so that the feed screw 52 fitted through the screw hole 50a reciprocates up and down.

A pump 53 generates sucking and discharging forces, and includes a cylinder 54 and a piston 56 reciprocative in the cylinder 54. The lower end of the feed screw 52 is coupled to the piston 56 in the cylinder 54. Due to the aforementioned reciprocative movement, the feed screw 52 moves the piston 56 up and down.

A disposable pipet tip 58 is attached to the lower end of the cylinder 54. The pipet tip 58 is detached from the cylinder 54 to replace the blood sample with a new one.

A slit disc 60 as an encoder disc is fixedly secured to the rotor 50. The slit disc 60 is inserted into a groove of a photo-interrupter 62. The photo-interrupter 62 emits light from one side of the slit disc 60, receiving the light passing through the slit disc 60 on the other side thereof. The slit disc 60 and photo-interrupter 62 constitute a rotation detector 64 to detect the rotative amount of the rotor 50. The detector operating signal 103 is supplied to the photo-interrupter 62. The photo-interrupter 62 includes an encoder.

The rotative amount of the rotor 50, the piston stroke and the drop volume of the blood are directly related to each other. In other words, the volume of the blood sample actually dropped can be determined based on the rotative amount of the rotor 50.

The pulse signal 101, i.e. the output of the photo-interrupter 62, is sent to the drop calculating circuit 30 of FIG. 1. In other words, the pulse signal 101 serves as a rotation detecting signal indicating the stroke of the piston 52. The drop calculating circuit 30 determines the drop volume of the blood sample based on the pulse signal 101.

Figure 2:
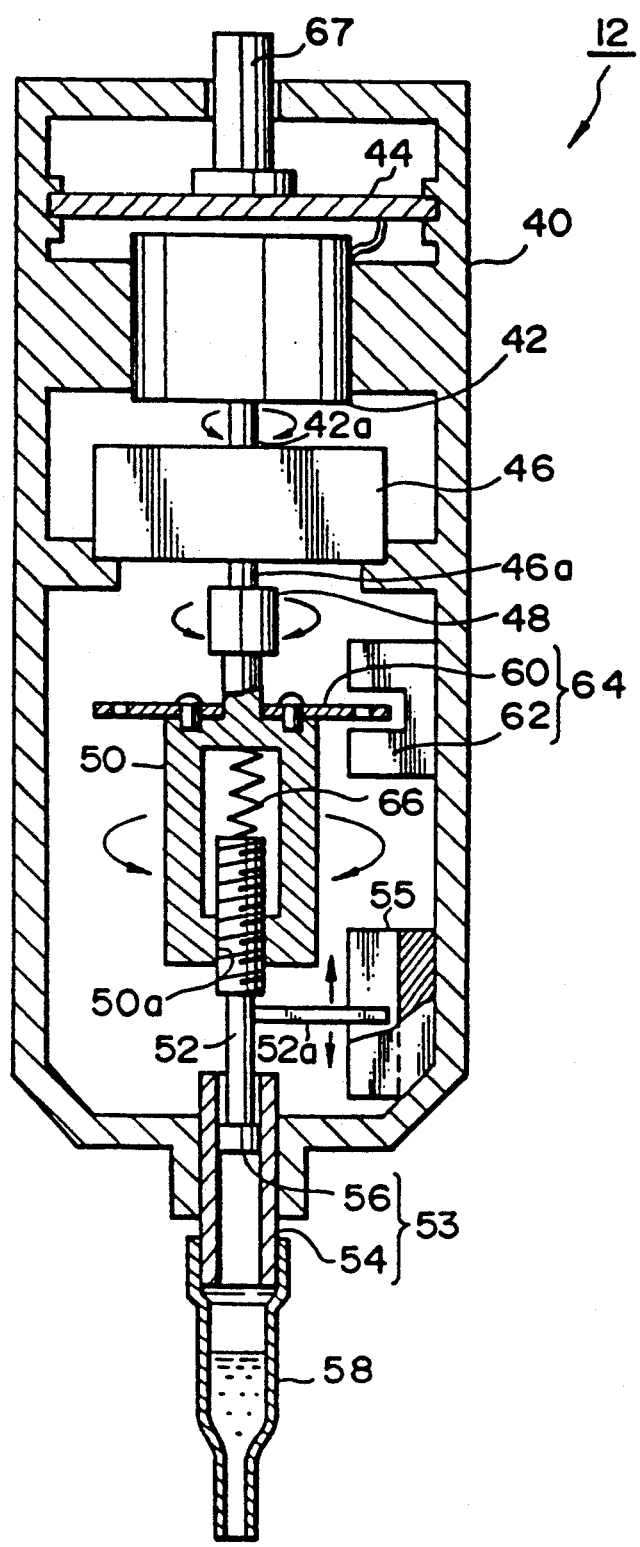
FIG. 2 is a cross-sectional view of a pipet unit.

As shown in FIG. 2, a spring 66 is located between the upper end of the feed screw 52 and a ceiling of the rotor 50. The spring 66 always urges the feed screw 52 downwardly in the rotor 50 to remove the backlash caused by engagement of the feed screw 52 with the screw hole 50a.

Under this condition, there still remains the backlash caused by the gear 46. In this embodiment, since the slit disc 60 is located on the rotor 50 (i.e. on the output side of the gear 46), the rotation detector 64 can reliably detect the rotation error of the rotor 50 due to the backlash appearing on the output shaft 46a. As described above, the spring 66 serves to remove the backlash between the screw hole 50a and the feed screw 52.

Therefore, the rotative amount of the rotor 50, i.e. the drop volume of the blood sample, can be accurately detected by the rotation detector 64. The accurately detected drop volume can be regarded as the volume of the blood actually dropped.

The pipet unit 12 will be operated as follows. The pipet tip 58 is inserted into the test tube containing the blood sample. When a switch 67 is operated, the motor 42 is rotated under the control of the main controller 34. The rotation speed of the motor 42 is reduced by the gear 46, so that the rotor 50 is rotated at the reduced velocity. Under this condition, the feed screw 52 is moved upwards to ascend the piston 56. The upward movement of the piston 56 decreases the pressure in the cylinder 54, so that the pipet tip 58 sucks the blood sample. The volume of the sucked blood is measured by the rotation detector 64.

Then, the pipet unit 12 is positioned above the test slide 14 shown in FIG. 1. The motor 42 is reversely rotated to descend the piston 52 and to drop the blood sample onto the test slide 14. The level of content of the component of the blood sample is measured according to the described procedure. The measured content will be corrected depending upon the volume of the blood sample actually dropped.

Figure 3:
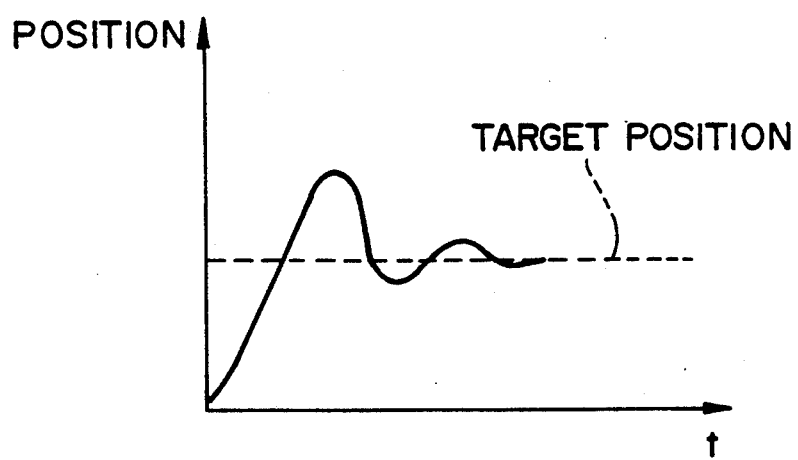
FIG. 3 is a graph showing positional variations of a piston.

FIG. 3 is a graph showing variations of the piston stroke with the lapse of time. When the piston 56 is moved so as to be stopped at the target position but deviates from it, the drop volume (or sucked volume) in response to the deviation can be accurately detected by the rotation detector (64), thereby assuring very precise analysis of the level of content of the specified component of the blood sample.

What is claimed is:

1. A blood analyzing system for analyzing the level of content of a component of a blood sample dropped onto a test slide, comprising:
   (a) a pipet unit for dropping the blood sample the blood sample having a predetermined desired dropped volume, said pipet unit including a pump having a cylinder and a piston;
   (b) a stroke meter for measuring the stroke of said piston and for outputting a stroke signal indicating a measured volume of the dropped blood sample, said stroke meter provided in said pipet unit wherein said pipet unit includes a motor for generating power to reciprocate said piston in said cylinder, a gear coupled to a rotary shaft of said motor, and a piston actuator for converting rotary motion of an output shaft of said gear into a rectilinear motion to reciprocate said piston, said piston actuator including a rotor coupled to said output shaft of said gear, a feed screw whose one end is coupled to said piston, and a rotation preventing member for allowing only the reciprocation of said feed screw while preventing the rotation thereof, said rotor being threadably engaged with the other end of said feed screw, said rotor being rotated by said output shaft to reciprocate said screw, said stroke meter determining the volume of the dropped blood sample based on the rotative amount of said rotor, said stroke meter including a slit disc rotatable with said rotor, and a photointerrupter for emitting light from one side of said slit disc and receiving the light from another side of said slit disc, said slit disc and said photo-interrupter comprising a rotation detector for determining rotor rotation indicative of a stroke of said piston;
   (c) a drop calculating circuit for receiving the stroke signal, calculating the volume of the dropped blood sample, and outputting a signal indicating the measured volume of the dropped blood sample;
   (d) a light source for irradiating light to the test slide holding the dropped blood sample;
   (e) an optical sensor for receiving the light reflected from the test slide and outputting a received light signal;
   (f) a content calculating circuit for receiving the signal indicating the measured volume of the dropped blood sample, and determining the level of content of the component of the blood sample, the analyzing system further including error determining means for determining an error between the desired and the measured dropped volumes, correction value obtaining means for obtaining a correction value from a correction table based on the determined error and correcting means for correcting the determined content level based on the obtained correction value; and
   (g) a backlash preventing means for supplying a bias force to said feed screw from said rotor, said backlash preventing means enabling reliable determination of the rotative amount of said rotor.

2. A blood analyzing system according to claim 1, further including a translation table which stores the relationship between the intensity of the received light signal and the level of content of the specified component, wherein the correction table stores correction coefficients for the measured volume of the dropped blood sample and the level of content of the specified component of the blood sample, so that said content calculating circuit calculates the level of content of the specified component of the blood sample with reference to said translation table, and corrects calculated result with reference to said correction table when the measured volume of the dropped blood sample deviates from the predetermined drop volume.

3. The blood analyzing system according to claim 1, wherein said content calculating circuit compares said signal indicating the measured volume of the dropped volume with a predetermined volume, said content calculating circuit correcting a calculated result when said dropped volume does not equal said predetermined volume.

4. A blood analyzing system according to claim 1, wherein said motor, said gear, said feed screw and said piston are linearly aligned.

5. A blood analyzing system according to claim 4, wherein said pipet unit includes a switch 6. A blood analyzing system for analyzing the level of content of a component of a blood sample dropped onto a test slide, comprising:
   (a) a pipet unit for dropping said blood sample in response to a desired dropped volume signal indicative of a desired dropped volume of the blood sample;
   (b) a drop meter for measuring a volume of the dropped blood sample and outputting a measured drop volume signal, said drop meter being provided in said pipet unit, said pipet unit including a pump having a cylinder and a piston, a motor for generating power to reciprocate said piston in said cylinder, a gear coupled to a rotary shaft of said motor, and a piston actuator for converting rotary motion of an output shaft of said gear into a rectilinear motion to reciprocate said piston, said piston actuator including a rotor coupled to said output shaft of said gear, a feed screw whose one end is coupled to said piston, and a rotation preventing member for allowing only the reciprocation of said feed screw while preventing the rotation thereof, said rotor being threadably engaged with the other end of said feed screw, said rotor being rotated by said output shaft to reciprocate said screw, said drop meter determining the volume of the dropped blood sample based on the rotative amount of said rotor, said drop meter including a slit disc rotatable with said rotor, and a photo-interrupter for emitting light from one side of said slit disc and receiving the light from another side of said slit disc, said slit disc and said photo-interrupter comprising a rotation detector for determining rotor rotation indicative of a stroke of said piston;

(c) a light source for irradiating light to the test slide holding the dropped blood sample;

(d) an optical sensor for receiving the light reflected from the test slide and outputting a received light signal;

(e) an analyzing unit for receiving the received light signal and the drop volume signal to determine the level of content of the component of the blood sample, the analyzing system further including error determining means for determining an error between the desired and the measured dropped volumes, correction value obtaining means for obtaining a correction value from a correction table based on the determined error and correcting means for correcting the determined content level based on the obtained correction value; and (f) a backlash preventing means for supplying a bias force to said feed screw from said rotor, said backlash preventing means enabling reliable determination of the rotative amount of said rotor.

7. A blood analyzing system according to claim 6, wherein said motor, said gear, said feed screw and said piston are linearly aligned.

8. A blood analyzing system according to claim 6, wherein said pipet unit includes a switch.

* * * * *